United States Patent [19]

Binder et al.

[11] Patent Number: 4,929,616
[45] Date of Patent: May 29, 1990

[54] NOVEL BASIC-SUBSTITUTED 5-HALO-THIENOISOTHIAZOL-3(2H)-ONE 1,1-DIOXIDES, A PROCESS FOR THE PREPARATION THEREOF, AND PHARMACEUTICAL PREPARATIONS CONTAINING THESE COMPOUNDS

[75] Inventors: Dieter Binder, Wien; Franz Rovensky, Bruck an der Leitha, both of Austria

[73] Assignee: Chemisch Pharmazeutische Forschungsgesellschaft, Linz, Austria

[21] Appl. No.: 306,744

[22] Filed: Feb. 6, 1989

[30] Foreign Application Priority Data

Feb. 18, 1988 [AT] Austria .................................. 390/88

[51] Int. Cl.$^5$ .................. A61K 31/505; C07D 521/00
[52] U.S. Cl. ...................................... 514/253; 544/295
[58] Field of Search ................. 544/295; 514/252, 253

[56] References Cited

U.S. PATENT DOCUMENTS 4,675,403  6/1987  Abou-Gharbia et al. ........... 544/295
4,732,984  3/1988  Abou-Gharbia et al. ........... 544/295
4,818,756  4/1989  Seidel et al. ......................... 544/295

FOREIGN PATENT DOCUMENTS 364852  11/1981  Austria .

Primary Examiner—Glennon H. Hollrah
Assistant Examiner—James H. Turnipseed
Attorney, Agent, or Firm—Wenderoth, Lind & Ponack

[57] ABSTRACT

The invention relates to a novel basic-substituted 5-halo-thienoisothiazol-3(2H)-one 1,1-dioxide of the formula

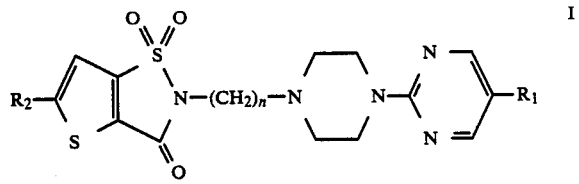

in which
$R_1$ denotes hydrogen, $(C_1-C_4)$-alkyl or halogen,
$R_2$ denotes halogen, and
n denotes an integer from 2 to 6, the pharmaceutically acceptable acid-addition salt thereof, a process for their preparation, and their use in medicament for the treatment of anxiety states.

4 Claims, No Drawings

NOVEL BASIC-SUBSTITUTED 5-HALO-THIENOISOTHIAZOL-3(2H)-ONE 1,1-DIOXIDES, A PROCESS FOR THE PREPARATION THEREOF, AND PHARMACEUTICAL PREPARATIONS CONTAINING THESE COMPOUNDS

DESCRIPTION

The invention relates to novel basic-substituted 5-halo-thienoisothiazol-3(2H)-one 1,1-dioxides, a process for the preparation thereof, pharmaceutical preparations containing these compounds, and the use thereof in medicaments for treatment of anxiety states.

U.S. Pat. No. 4,732,984 disclosed anxiolytically active 4-(1-piperazinyl)butylthieno- and -benzoisothiazol-3(2H)-ones, where the thieno compounds are unsubstituted on the thiophene ring. Novel thienoisothiazol-3(2H)-ones were found which are substituted in the 5-position on the thiophene ring by halogen and which have superior activity to the unsubstituted thiophene compounds mentioned in U.S. Pat. No. 4,732,984.

The invention therefore relates to novel compounds of the formula I

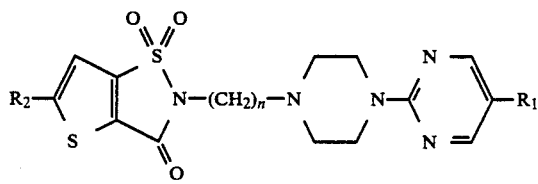

in which $R_1$ denotes hydrogen, $(C_1-C_4)$-alkyl or halogen,
$R_2$ denotes halogen and
n denotes an integer from 2 to 6, the pharmaceutically acceptable acid-addition salts thereof, a process for their preparation, pharmaceutical preparations which contain these compounds, and the use thereof in medicaments for treatment of anxiety states.

The term $(C_1-C_4)$-alkyl includes all straight-chain and branched saturated hydrocarbon radicals having 1–4 carbon atoms, such as, for example, methyl, ethyl, propyl, isopropyl, and tert. butyl. Halogen is taken to mean chlorine, bromine or iodine.

The compound 5-chloro-2-(4-(4-(2-pyrimidinyl)-1-piperazinyl)butyl)thieno(2,3-d)isothiazol-3(2H)-one 1,1-dioxide is particularly preferred.

The compounds of the formula I and the salts thereof are prepared by reacting a compound of the formula II

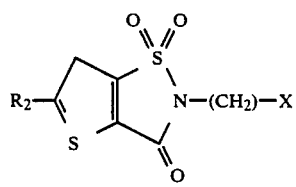

in which $R_2$ and n are as defined above and X denotes halogen, with a compound of the formula III

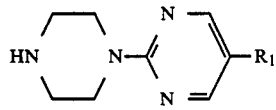

in which $R_1$ is as defined above, and, if desired, converting the bases of the formula I obtained into a pharmaceutically acceptable acid-addition salt.

The reaction of a compound of the formula II

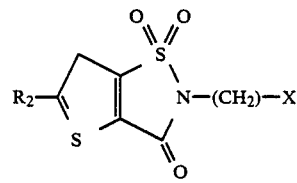

with a compound of the formula III

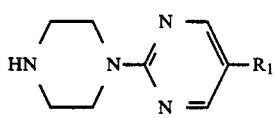

is carried out in a diluent which is inert under the reaction conditions. To this end, a compound of the formula II is dissolved in an organic diluent, such as, for example, DMF, DMSO, chlorobenzene, diethyl carbonate or acetone, a solution of a compound of the formula III in the same solvent is added dropwise, and the mixture is allowed to react to completion with stirring. The reaction time here is between 30 minutes and 15 hours at a temperature of from 20° to 150° C., preferably at 50° to 70° C., higher reaction temperatures meaning shorter reaction times and vice versa.

The compounds of the formula I obtained are worked up in a customary manner by evaporation, precipitation, precipitation as a salt, extraction, recrystallization or by column chromatography. Extraction of the crude product from the aqueous phase by means of methylene chloride has proven successful in this case. Since the free bases of the formula I are substances which can be purified only with difficulty, it is advisable to carry out the purification via readily crystallizing acid-addition compounds.

To this end, the free base is dissolved in a suitable solvent, for example in a low alcohol or ether or in acetone, and an at least equivalent amount of a protonic acid, such as, for example, HCl, HBr, $H_2SO_4$, tartaric acid or citric acid, is added. The mixture is evaporated if necessary, and the product is crystallized from methanol, ethanol, isopropanol, n-propanol or acetone, if necessary with addition of ether.

These acid-addition salts can be converted into the free bases in a manner known per se, for example using alkalis or ion exchangers; further salts can be obtained from these bases by reaction with inorganic or organic pharmaceutically acceptable acids.

Pharmaceutically acceptable salts are, for example, salts with inorganic acids, such as, for example, hydrochloric acid, hydrobromic acid, sulfuric acid, phosphoric acid or nitric acid, or with organic acids, such as citric acid, tartaric acid, maleic acid, fumaric acid, succinic acid, maleic acid, methanesulfonic acid, aminosulfonic acid, acetic acid, benzoic acid and the like.

The compounds for the formula II

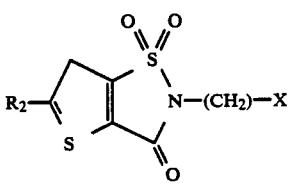

can be prepared by customary chemical procedures which are known to those skilled in the art in accordance with reaction scheme I

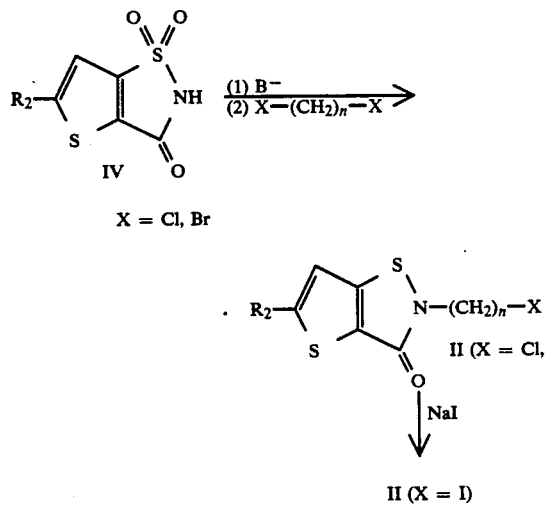

X = Cl, Br starting from the compounds of the formula IV.

The compounds of the formula IV are substantially known from the literature (U.S. Pat. No. 4,028,373, U.S. Pat. No. 4,233,333, U.S. Pat. No. 4,430.355). Those which were hitherto unknown can be prepared from the compounds of the formulae V and VI which are described in the literature (U.S. Pat. No. 4,076,709, U.S. Pat. No. 4,134,898, U.S. Pat. No. 4,177,193, U.S. Pat. No. 4,224,445, U.S. Pat. No. 4,230,873, U.S. Pat. No. 4,187,303, U.S. Pat. No. 4,180,662 and U.S. Pat. No. 4,544,655), in accordance with reaction scheme II The novel compounds of the formula I and their pharmaceutically usable salts exhibit excellent anxiolytic properties in appropriate animal models.

Due to these pharmacological properties, the novel compounds, alone or mixed with other active substances, can be used in the form of customary galenic preparations for the treatment of various anxiety states without causing hypnotic-sedative side effects.

The compounds of the formula I are intended for human use and can be administered in a customary manner, such as, for example, orally or parenterally. They are preferably administered orally, the daily dose being about 0,01 to 10 mg/kg of body weight, preferably 0,05 to 0,5 mg/kg of boy weight. In the case of intravenous administration, the daily dose is about 1,0 tp 50 mcg/kg of body weight, preferably about 10 mcg/kg of body weight. However, the doctor carrying out the treatment may also prescribe doses above and below this level, depending on the general state and the age of the patient, the particular substance of the formula I, the nature of the disease and the type of formulation.

The compounds of the formula I can be administered alone or in combination with other pharmaceutically active substances, the content of the compounds of the formula I being approximately between 0.1 and 99%. In general, the pharmaceutically active compounds are in the form of a mixture with suitable inert adjuvants and/or carriers or diluents, such as, for example, pharmaceutically acceptable solvents, gelatin, gum arabic, lactose, starch, magnesium stearate, talc, vegetable oils, polyalkylene glycol, vaseline and the like.

The pharmaceutical preparations can be in solid form, for example as tablets, coated tablets, suppositories, capsules and the like, in semi-solid form, for example as ointments, or in liquid form, for example as solutions, suspensions or emulsions. If appropriate, they are sterilized and contain adjuvants, such as preservatives, stabilizers or emulsifiers, salts for modifying the osmotic pressure, and the like.

In particular, pharmaceutical preparations can contain the compounds according to the invention in combination with other therapeutically useful substances. With these, the compounds according to the invention can be formulated, for example, together with the above-mentioned adjuvants and/or carriers or diluents, to form combination preparations.

The abbreviations used in the examples below have

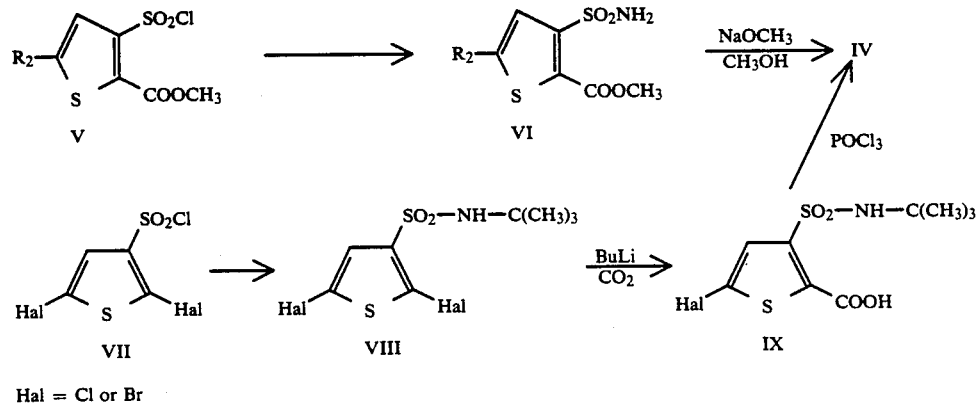

Hal = Cl or Br

The compounds of the formula III are known from the literature (K. L. Howard, H. W. Stewart, E. A. Conroy and J. J. Denton, J. Org. Chem. 18, 1484(1953).

the following meanings:

| | |
|---|---|
| Ti | Thienoisothiazole |
| Pyr | Pyrimidine |
| Pip | Piperazine |

EXAMPLE 1

5-Chloro-2-(4-(4-(2-pyrimidinyl)-1-piperazinyl)-butyl)-thieno-(2,3-d)isothiazol-3(2H)-one 1,1-dioxide 25 ml of absolute dimethylformamide are added to 5.5 g (13.6 mmol) of 2-(4-iodobutyl)-5-chlorothieno(2,3-d)isothiazol-3(2H)-one 1,1-dioxide, and the solution is warmed to 40° C. 2.23 g (13.6 mmol) of 1-(2-pyrimidinyl)-piperazine are then dissolved in absolute dimethylformamide at 60° C. and added to the solution over the course of one minute. After 45 minutes at 60° C., the solvent is evaporated, and the oily orange residue is taken up in 25 ml of methylene chloride. The methylene chloride phase is washed by shaking twice with 20 ml of water in each case and subsequently extracted eight times with a total of 130 ml of 2N hydrochloric acid. The acidic aqueous phase is neutralized using solid sodium bicarbonate (pH=7.5) and then extracted by shaking four times with 25 ml of methylene chloride in each case. The combined organic phases are dried over sodium sulfates, filtered and evaporated. The crude product obtained (4.0 g; 57% of theory) is dissolved in 45 ml of boiling isopropanol, and a small amount of insoluble byproduct (70 mg) is filtered off from the hot solution. The mother liquor is left to crystallize in the freezer with repeated trituration, and the yellow product is then filtered off with suction and digested three times with ice-cold isopropanol. The crude product obtained (3.3 g; 7.67 mmol) is dissolved in 35 ml of boiling acetone, and the solution is filtered and cooled with stirring, and 0.93 g (7.67 mmol) of 29.2% strength methanol hydrochloric acid is added. The hydrochloride is allowed to crystallize in the freezer with repeated trituration, and is filtered off with suction and digested three times with a little ice-cold acetone. The 2.93 g of hydrochloride, dried at 40° C./20 mbar, are suspended in 45 ml of water, adjusted to a pH of 7.5 using saturated sodium bicarbonate solution and extracted four times with 30 ml of methylene chloride in each case. The combined organic phases are dried over sodium sulfate, activated charcoal is added, the mixture is filtered, and the solvent is evaporated (2.75 g of product). The final purification is carried out by column chromatography (silica gel 60; 50:1; eluent: diethyl ether). The product is again recrystallized from 25 ml of isopropanol.

Yield: 2.25 g of pale yellow crystals (38% of theory).
M.p.: 134°-135.5° C. (isopropanol).

Microelemental analysis:
$C_{17}H_{20}N_5ClO_3S_2$ MW = 441.96

| | C | H | N |
|---|---|---|---|
| Calculated | 46.20 | 4.56 | 15.85 |
| Found | 46.04 | 4.62 | 15.70 |

$^1$H-NMR: (CDCl$_3$) delta (ppm): 8.29 (d; I=4.9 Hz; 2H, Pyr-H$_4$ and H$_6$), 7.28 (s; 1H; Ti-H$_6$), 6.47 (t; I=4.9 HZ; 1H; Pyr-H$_5$), 3.90-3.70 (m; 6H; pip-H$_3$ and H$_5$, Ti—CH$_2$—), 2.56-2.36 (m; 6H; pip-H$_2$ and H$_6$, —CH$_2$-pip), 2.00-1.50 (m; 4H; Ti—C—CH$_2$—and —CH$_2$—C-pip-).

The starting material can be prepared as follows:

2-(4-Bromobutyl)-5-chlorothieno(2,3-d)isothiazol-3(2H)-one 1,1-dioxide 15 g (67.1 mmol) of 5-chlorothieno(2,3-d)isothiazol-3(2H)-one 1,1-dioxide are dissolved in 100 ml of absolute dimethylformamide. 2.82 g (70.5 mmol) of 60% strength sodium hydride suspension are then washed four times with absolute benzene and added to the DMF solution with ice cooling and vigorous magnetic stirring at a sufficiently slow rate that the temperature does not exceed 15° C. The reaction mixture is stirred at room temperature for 15 minutes and then heated to 60° C., and 43.5 g (202 mmol) 1,4-dibromobutane are added over the course of 30 minutes. After three hours at 60° C., the solution is evaporated at 70° C./1.5 mbar. The yellow oil remaining is suspended in 40 ml of saturated sodium bicarbonate solution and extracted three times with 50 ml of methylene chloride in each case. The combined organic phases are then re-shaken twice with 50 ml of saturated sodium bicarbonate solution in each case and twice with a total of 110 ml of water. The organic phase is dried over sodium sulfate, activated charcoal is added, and the mixture is filtered and evaporated. The crude product is dissolved in 100 ml of boiling diethyl ether, and 500 mg of colorless of byproduct are filtered off with suction. After evaporation of the solvent, 19.74 g of solid crude product remain and can be employed in the next reaction step without further purification. 0.7 g is subjected to purification by column chromatography (silica gel 60; 40:1, eluent: methylene chloride; yield 0.62 g).

Yield: 17.48 g of colorless crystals (73% of theory).
M.p.: 75°-76° C. (diethyl ether).

2-(4-Iodobutyl)-5-chlorothieno(2,3-d)isothiazol-3(2H)-one 1,1-dioxide.

2.3 g (15.3 mmol) of sodium iodide are dissolved in 70 ml of absolute acetone, and 5.5 g (15.3 mmol) of 2-(4-bromobutyl)-5-chlorothieno-2,3-d)isothiazol-3(2H)-one 1,1 dioxide are added in one portion. The mixture is refluxed for 90 minutes with vigorous magnetic stirring, a colorless, voluminous precipitate being produced. The reaction mixture is evaporated, taken up in 40 ml of methylene chloride and extracted twice with 60 ml of saturated sodium bisulfite solution in each case. The methylene chloride phase is re-shaken with 25 ml of water. The organic phase is dried over sodium sulfate, filtered and evaporated. The crude product can be employed directly in the next step. 1 g of crude product is purified by column chromatography (silica gel 60; 30:1; eluent: methylene chloride:petroleum ether=2:1; yield 0.94 g).

Yield: 5.57 g of pale yellow crystals (90% of theory)
M.p.: 86°-87° C. (methylene chloride).

EXAMPLE 2: (Comparative example)

According to example 1 the following substance was prepared:

2-(4-(4-(2-Pyrimidinyl)-1-piperazinyl)butyl)thieno-(2,3-d)isothiazol-3(2H)-one 1,1 dioxide
Fp: 117°-118° C. (isopropanol).
What we claim is:
1. A compound of the formula

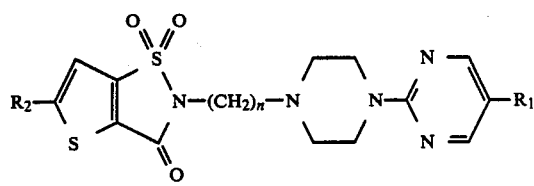

in which

R₁ denotes hydrogen, (C₁–C₄)-alkyl or halogen,

R₂ denotes halogen, and n denotes an integer from 2 to 6, and the pharmaceutically acceptable acid-addition salts thereof.

2. 5-Chloro-2-(4-(4-(2-pyrimidinyl)-1-piperazinyl)-butyl)-thieno-(2,3-d)isothiazol-3(2H)-one 1,1-dioxide.

3. A pharmaceutical composition comprising a compound of the formula

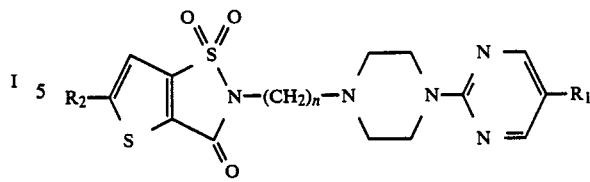

defined in claim 1 or a pharmaceutically acceptable salt thereof, in an anxiolytically effective amount for the treatment of anxiety states in humans in combination with a pharmaceutically acceptable excipient, carrier or diluent.

4. A method for the treatment of anxiety states in humans which comprises administering to a patient an anxiolytically effective amount of a compound of the formula

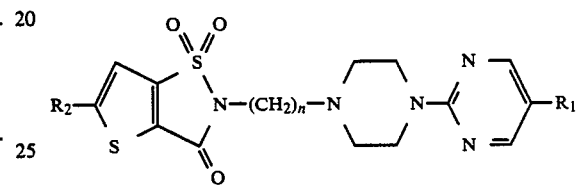

defined in claim 1 or a pharmaceutically acceptable salt thereof, in combination with a pharmaceutically acceptable excipient, carrier or diluent.

* * * * *